(12) United States Patent
Frey et al.

(10) Patent No.: US 8,372,091 B2
(45) Date of Patent: Feb. 12, 2013

(54) DEVICE FOR MOVING A THREAD OF A SURGICAL SEWING INSTRUMENT

(75) Inventors: Sebastian Frey, Waghaeusel (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1037 days.

(21) Appl. No.: 12/257,117

(22) Filed: Oct. 23, 2008

(65) Prior Publication Data

US 2009/0112235 A1   Apr. 30, 2009

(30) Foreign Application Priority Data

Oct. 24, 2007   (DE) .................. 10 2007 052 195

(51) Int. Cl.
*A61B 17/04* (2006.01)
(52) U.S. Cl. ........................................................ 606/146
(58) Field of Classification Search .................. 606/103, 606/139, 144–148, 201, 227, 232; 132/323; 298/17
See application file for complete search history.

(56) References Cited

U.S. PATENT DOCUMENTS

| | | | | |
|---|---|---|---|---|
| 3,587,587 A | * | 6/1971 | Raskin | 606/146 |
| 4,890,615 A | * | 1/1990 | Caspari et al. | 606/146 |
| 4,935,027 A | | 6/1990 | Yoon | |
| 4,957,498 A | | 9/1990 | Caspari et al. | |
| 5,254,126 A | | 10/1993 | Filipi et al. | |
| 5,704,943 A | * | 1/1998 | Yoon et al. | 606/139 |
| 2005/0283171 A1 | | 12/2005 | Bellafiore et al. | |
| 2006/0229642 A1 | | 10/2006 | Oberlaender et al. | |
| 2007/0179510 A1 | | 8/2007 | Stone | |

FOREIGN PATENT DOCUMENTS

DE   102005015687 A1   10/2006
GB   630693 A   10/1949

OTHER PUBLICATIONS

Catalog, "Arthroscopy, Sports Medicine, Spinal Surgery," 2nd edition Jan. 2005, p. 106 (Bulletin ART-SHF 14A) by Karl Storz Gmbh & Co. KG, Tuttlingen, Germany ( 4 pages).
European Search Report; EP 08 16 7345; Apr. 6, 2009; 7 pages.

* cited by examiner

*Primary Examiner* — Corrine M McDermott
*Assistant Examiner* — Christina Lauer
(74) *Attorney, Agent, or Firm* — St. Onge Steward Johnston & Reens LLC

(57) ABSTRACT

A device (10) is used for moving a thread of a surgical sewing instrument (60). The device comprises a clamp (18) for detachably clipping said device (10) on the surgical sewing instrument (60). The device has an arm (24) having a first end connected to said clamp (18). A freely rotatable roller (50) being arranged at a second end of said arm (24), said roller (50) resting on the thread of the surgical instrument (60) having clipped on the device (10).

26 Claims, 5 Drawing Sheets

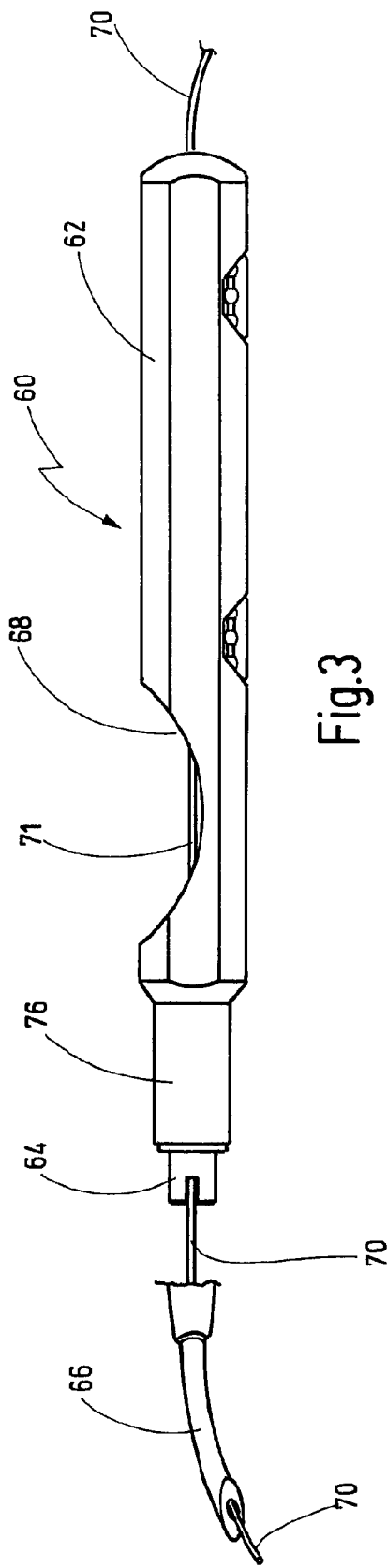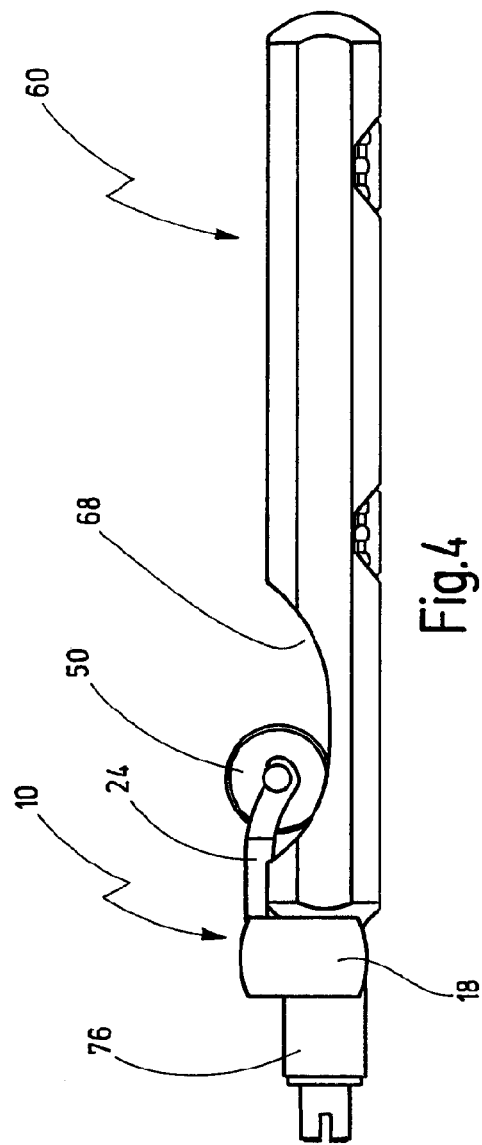
Fig.3
Fig.4

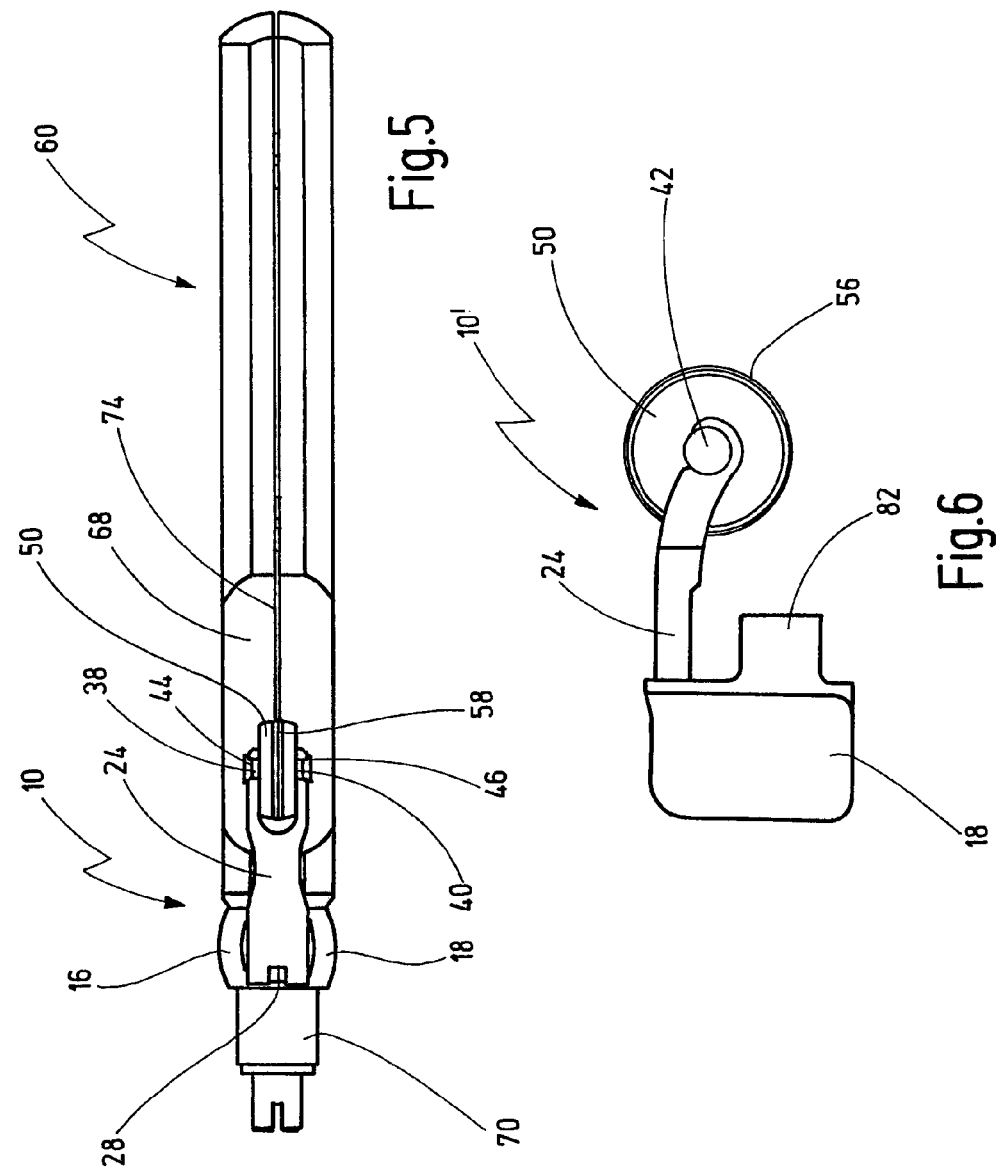

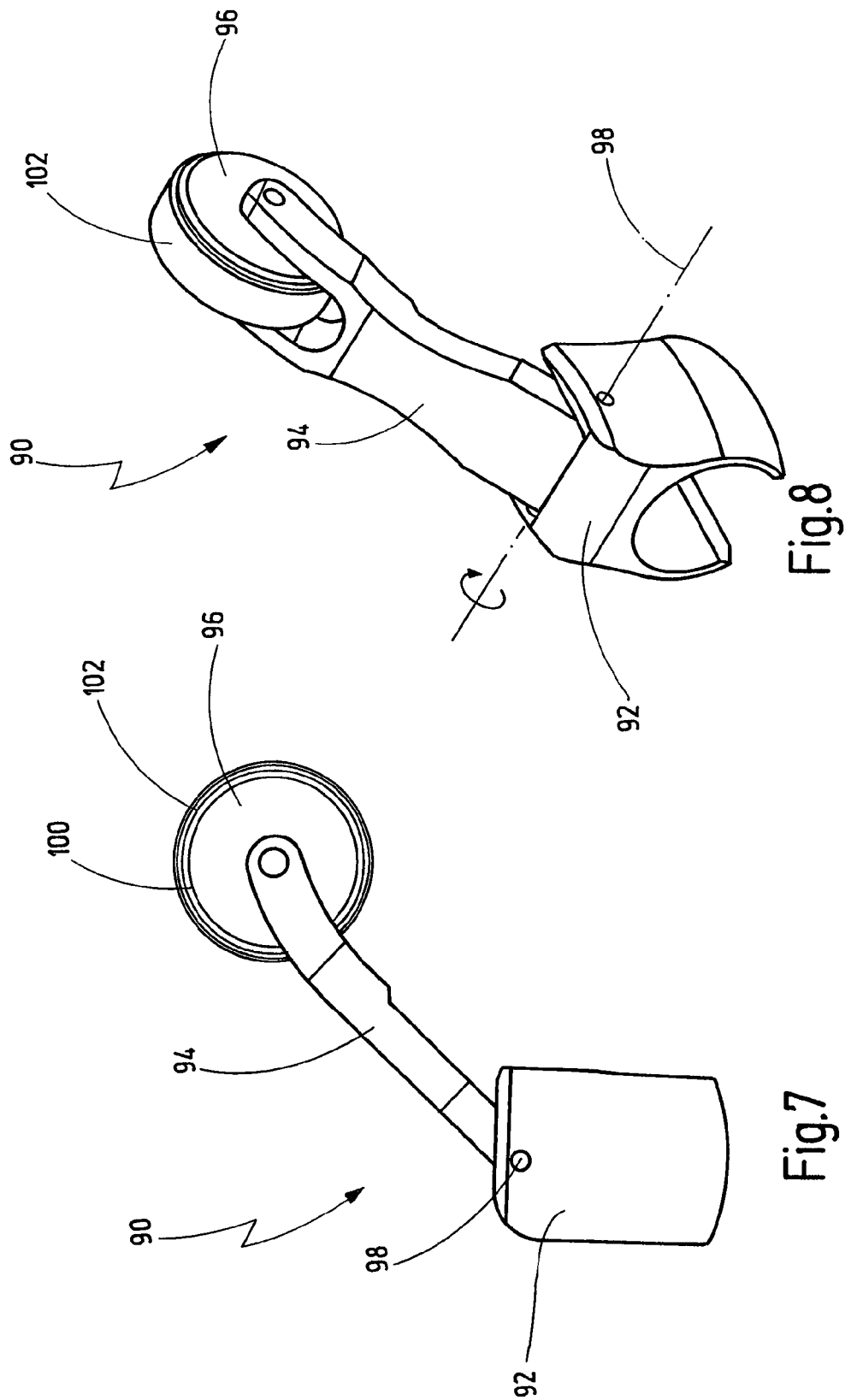

DEVICE FOR MOVING A THREAD OF A SURGICAL SEWING INSTRUMENT

BACKGROUND OF THE INVENTION

The invention relates to a device for moving a thread of a surgical sewing instrument, in which the thread can be moved directly by one finger of a hand of an operator.

The invention further relates to a surgical sewing instrument provided with such a device for moving a thread.

A device for guiding surgical sewing material to a needle is known from US 2006/0229642 A1.

This surgical sewing instrument has an approximately rod-like body, through which a surgical thread can be guided from a proximal to a distal end where a suture attachment is disposed. The rod-like body has a recess, along which a section of the thread is guided exposed. The hollow or recess is adapted in that a thumb of a hand of an operator holding the rod-like body can be inserted into the recess thereby touching the section of the thread exposed in the area of the recess.

This enables the operator to move the thread reciprocally by a finger.

For example he can shift the thread by moving the finger from proximal to distal thereby moving the thread out of the distal end of the needle attachment.

Many surgical threads are very smooth due to their structure on the outside such that reciprocal motion of the thread is made difficult. This can be further aggravated by the hand of the operator, normally covered by a latex glove, slipping over the thread.

If the glove is contaminated with liquids, for example blood, a secure moving of the thread is not possible.

U.S. Pat. No. 4,890,615 discloses an arthroscopic suturing instrument. The suturing instrument for use in arthroscopic surgery includes a hollow needle for penetrating tissue to be sutured within a body while the tissue is clamped between relatively movable jaws. A suture feed mechanism is provided for feeding suture material through the hollow needle such that the jaws can be opened and the suturing instrument withdrawn from the body pulling the free end and segment of the suture material with the instrument. The suture material feed mechanism has two rollers converging via their peripheral surfaces which are mounted fixedly on one of the two grips of the medical instrument. A thread can be threaded in between the two rollers and guided by the long hollow shaft of the instrument as far as the distal sewing device. To move the thread one of the two rollers is exposed to an extent where this exposed roller can be rotated by a finger of a hand gripping the scissors-like instrument. When turning the roller the thread is moved between the two adjacent rollers depending on the direction of turning the outer exposed roller.

The structure of this feeding mechanism is very complicated, has countless single parts. Both rollers must be held and mounted in a separately mounted thread feed structure. This results in countless niches for bacteria, making cleaning and sterilizing very difficult.

It is therefore an object of the present invention to provide a simple thread feeding mechanism which is of simple construction.

It is a further object of the present invention to provide a thread feeding mechanism which can be used only if necessary i.e. if the structure of the outer surface of the thread is inconvenient for the operator for moving the thread directly with its finger.

It is quite a further object of the present invention to design a device which can be easily cleaned.

SUMMARY OF THE INVENTION

According of one aspect of the invention these objects are achieved by a device for moving a thread of a surgical sewing instrument comprising a clamp for detachably clipping the device on to a surgical sewing instrument, an arm having a first end connected to said clamp, a freely rotatable roller being arranged at a second end of said arm, said roller resting on a thread of a surgical instrument having clipped on said device.

An advantage of this device is that in case of need the device can be clipped on to the surgical sewing instrument.

There can be such a case of need for example if a thread which has an extremely smooth surface is to be moved. With a simple clip-on procedure the device can be attached to the rod-like body of the sewing instrument in such a way that the roller comes to rest on the exposed section of the thread. Rotating the roller can then move the thread.

As easily as the device can be clipped on, it can also be removed again from the surgical instrument, thereby a substantially simplifying cleaning and sterilizing. In contrast to the abovementioned U.S. Pat. No. 4,890,615 only a single roller and not two superposed rollers are used, as the motion of the thread occurs only via the one roller of the clipped-on device. The roller not only makes handling easier, but also threading of the thread into the instrument. When threading in the thread from the proximal end the thread achieves the recess where the thread is exposed. This bears the risk that during threading the thread moves laterally out of the recess and therefore cannot be fed to the distal end suture attachment. When the device is clipped on the sewing instrument this device further purposes for assisting the threading of the thread across of the recess.

With those thread materials which have a relatively rough surface or in the case of operators who have a good sense of feel through their glove for moving the thread, the device can be omitted. With other, particularly smooth, materials or if moisture reaches the thread during a surgery, the device can easily be clipped on and the moving of the thread can then be controlled by the roller of the clipped-on device. This results in a substantially simpler construction than with fixedly installed roller mechanisms as for example described in U.S. Pat. No. 4,890,615 which requires at least two rollers.

The invention allows substantially greater flexibility relative to the operator and the components are also substantially easier to clean. It is also possible for example to make the device from plastic materials as disposable items, obviating the need for a cleaning and sterilizing procedure.

The objects of the invention can also be achieved by a surgical sewing instrument having the above mentioned device clipped thereon.

In another configuration of the invention the roller is attached removably to the arm.

The advantage of this measure is that cleaning the device is substantially simplified. This also offers the possibility of using different rollers in one and the same device, for example with different linings on the peripheral side, to be able to individually match specially designed threads.

In another configuration of the invention the roller is held by two retaining arms of the arm.

The advantage of this measure is that the roller is held on the arm by structurally simple measures. This makes not only constructing the device easier, but also its subsequent cleaning.

In another configuration of the invention the roller can be clipped in to the arm.

The advantage of this measure is that the roller can be set into the arm by a simple clip-in procedure or removed therefrom to perform the abovementioned cleaning, sterilizing or replacement procedures.

In another configuration of the invention there are grooves in the two retaining arms, into which grooves ends projecting from both sides of a bearing shaft bearing said roller can be clipped.

The advantage of this measure is that the abovementioned advantages can be attained particularly easily. This also offers the possibility for example of designing the roller as a disposable item only, whereas the arm and the clamp are designed as reusable parts, i.e. only one new roller is in each case clipped in after use.

In another configuration of the invention a peripheral surface area of the roller is provided with material of high friction.

The advantage of this measure is that, first, contact between the finger, for the most part covered by a glove, and the roller is intensive and, secondly, contact between the roller and the thread to be transported.

In another configuration of the invention there is a circumferential slot in the roller, in which the thread can be taken up.

The advantage of this measure is that a guide for the thread is additionally provided by the slot in the roller.

In another configuration of the invention the slot is provided between two O-rings which are attached to the peripheral surface of the roller.

The advantage of this measure is that for example the material of high friction can be provided by the material of the O-rings and at the same time a slot for guiding the thread is configured between the latter. This also prevents the threads from being squashed and are no longer to be guided to the needle.

In another configuration of the invention the arm is attached pivotably on the clamp.

The advantage of this measure is that more or less strong pressure can be exerted on the thread by the operator via the pivot capacity of the arm, depending on how the operator wants to do this.

Pivoting also makes handling easier, for example when the thread is threaded in or when the device is placed or removed.

In another configuration of the invention the pivotable arm can be pivoted against the force of a spring.

The advantage of this measure is that the operator presses the arm against the force of a spring on the thread, giving better contact feel for the operator. At the same time, the force of the spring can be utilized to raise the arm automatically, i.e. it lifts up from the thread, such that corresponding manipulation such as for example threading in or the like can then be carried out without the roller having to be manually lifted from the thread.

In another configuration of the invention the pivotable arm can be fixed by a catch to the clamp.

The advantage of this measure is that the catch holds the arm in a position for example pivoted towards the handgrip.

In another configuration of the invention the clamp has a lock preventing a rotation of the device about the body of the instrument.

This is particularly advantageous if the device is clipped onto a rod-like body having an approximately round cross-section. Securing against rotation ensures that the device does not rotate during handling.

In another configuration of the invention the lock is designed as projections standing out from the clamp.

The advantage of this measure is that securing against rotation can be effected using simple components which can be provided for example as early as during the original manufacturing procedure, for example during injection-moulding as a plastic item.

In a configuration of the invention the device according to the invention can be connected as a set to a surgical sewing instrument, offered or sold, whereby the surgical sewing instrument has an approximately rod-like body, through which a surgical thread can be fed from proximal to distal to a suture attachment, with a recess in the body, along which a section of the thread is exposed, whereby the device according to the invention is attached such that the roller comes to rest on the exposed section of the thread in the recess.

Both the surgical sewing instrument and the clip-on device are now offered in this set, such that all variants can be executed, that is to say operation with or without the clipped-on device.

It is understood that the abovementioned characteristics and those yet to be explained hereinbelow can be used not only in the respectively specified combination, but also in other combinations, without departing from the scope of the present invention.

BRIEF DESCRIPTION OF THE DRAWINGS

The invention will now be described and explained in greater detail by means of some selected embodiments in connection with the attached diagrams, in which:

FIG. 3 shows a side elevation of a surgical sewing instrument, to which the device of FIGS. 1 and 2 can be clipped on, FIG. 4 shows a side elevation corresponding to FIG. 3, whereby the device of FIGS. 1 and 2 is clipped on, FIG. 5 shows a plan view of the assembly of FIG. 4, FIG. 6 shows a second embodiment of the device with a lock against rotation, FIG. 7 shows a side elevation of a third embodiment of a device according to the invention with a pivotable arm, though without pivoting capacity against the force of a spring, FIG. 8 shows a perspective view of the device of FIG. 7.

DETAILED DESCRIPTION OF PREFERRED EMBODIMENTS

Figure 1:
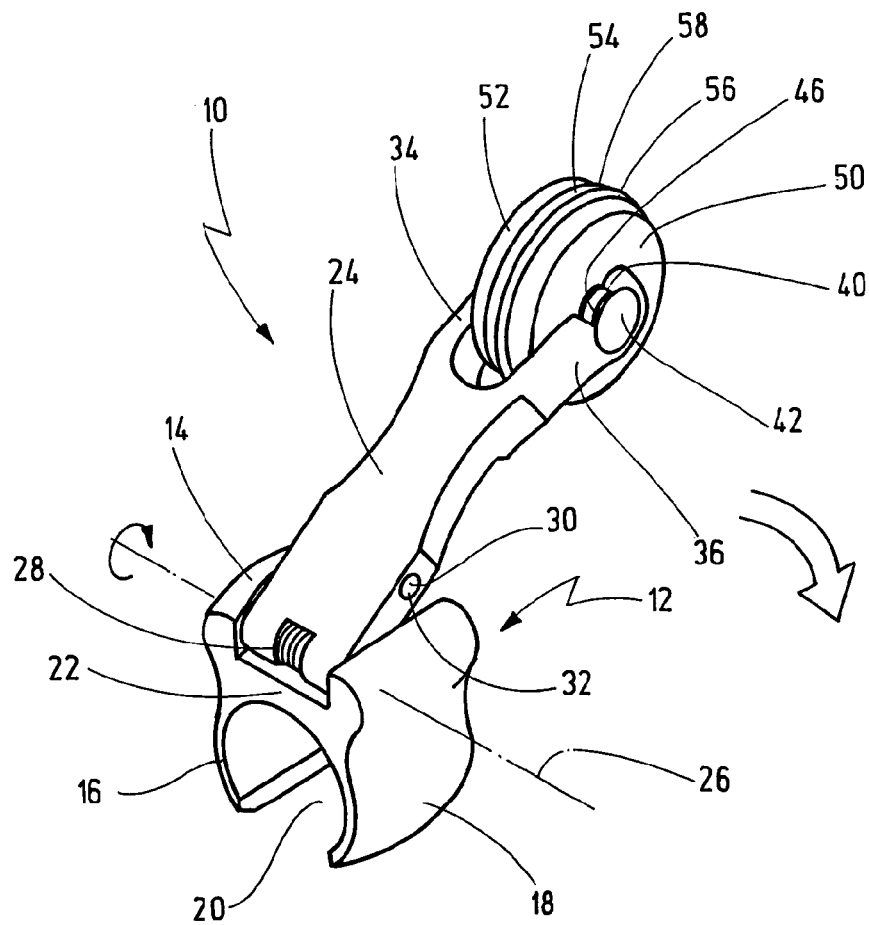
FIG. 1 shows a perspective view of a first embodiment of a device according to the invention, in which the arm can be set against the force of a spring.
Figure 2:
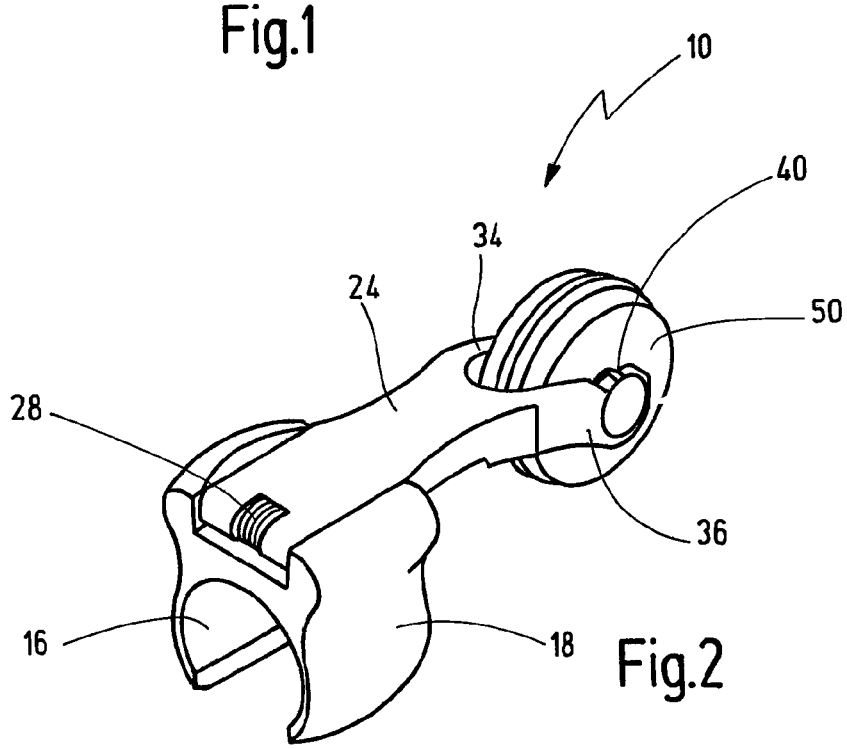
FIG. 2 shows the device of FIG. 1, whereby the pivotable arm is illustrated in a catched end position.

The first embodiment of a device according to the invention illustrated in FIGS. 1 and 2 is designated in its entirety by reference numeral 10.

The device 10 has a clamp 12 in the form of a U-shaped clamping piece 14. The clamping piece 14 has two bent protruding legs 16 and 18 which bound an opening 20. Both legs 16 and 18 are designed such that once they are briefly spread they can be clipped onto a body which approximately occupies the shape of the opening 20; the legs also firmly enclose this body after both legs or respectively the clamping piece 14 has been clipped onto this body.

An arm 24 is pivotably attached at a first end to a cross piece 22, connecting both legs 16 and 18 together. The arm 24 is mounted at a first end via an axial pin, not evident here in greater detail, such that it can pivot about an axis 26.

A spring 28 is laid about the axial pin which is pre-tensed such that it aligns the arm 24 in the alignment shown in FIG. 1. A leg of the spring 28 is supported for this purpose on the cross piece 22.

The arm 24 can thus be pivoted against the force of the spring 28 about the axis 26, for example into the position shown in FIG. 2. FIG. 1 shows that a catch 30 is provided to hold the arm 24 in the latched position illustrated in FIG. 2. The catch 30 has a ball latch 32, whereby in FIG. 1 the sphere of the ball latch is visible. A corresponding recess is present on the inside of the upper end of the leg 18, into which the sphere 32 can snap. This situation is shown in FIG. 2, i.e. in this situation the arm 24 is latched. To bring the arm 24 back to the illustrated position shown in FIG. 1 the force of the ball latch must first be overcome, after which the force of the spring 28 positions the arm 24.

At the second end opposite the axis 26 the arm 24 has two forked protruding retaining arms 34 and 36 which in each case have a groove 38 or 40. A bearing shaft 42 or respectively its ends 44 and 46 projecting to the side can be pressed into the grooves 38 and 40 (see FIG. 5). The bearing shaft 42 bears a roller 50. The roller 50 is freely rotatable about the bearing shaft 42.

A peripheral area 52 of the roller is fitted with two silicon O-rings 54 and 56 arranged at a distance from one another such that a slot 58 is configured between them.

A field of application of the device 10 is illustrated in FIGS. 3 to 5, specifically the use in connection with a surgical sewing device 60, as shown in FIG. 3. Such a surgical sewing device, as shown in FIG. 3, is marketed for example by the applicant under the product designation 28179 HG and is described in more detail in US 2006/0229642 A1 which is hereby incorporated by reference.

This surgical sewing device 60 has a rod-like body 62 which is designed as an elongated handgrip. Depending on what kind of sewing procedure is to be performed different sewing attachments 66 can be placed on the distal end 64. A recess 68, designed as a type of finger trough, is left open in the vicinity of this end in the body 62.

A surgical thread 70 can be threaded through the rod-like body 62 from proximal to distal, through which the suture attachment 66 is then also threaded, by which the sewing procedure is then executed. It is evident from the side elevation of FIG. 3 that a section 71 of the surgical thread 70 is exposed in the recess 68.

The surgical sewing device 60 can be operated in such a way that the rod-like body 62 is gripped by a hand such that the thumb of the hand for example comes to rest in the region of the recess 68, after the surgical thread 70 is threaded through and a correspondingly desired suture attachment 66 is set on. If the thumb is now laid on the section 71 of the thread 70 and moved reciprocally, the thread 70 can be moved reciprocally.

As shown in FIG. 4, to make this procedure easier and to support it the device 10 evident in FIGS. 1 and 2 is clipped onto a cylindrical extension 76 of the surgical sewing device 60, and in such a way that the roller 50 comes to rest on the section 71 of the surgical thread 70 which transits the recess 68.

The handling of the assembly of FIG. 4 is the same as previously described in connection with FIG. 3, i.e. a thread 70 is threaded through and a corresponding suture attachment 66 is set on, whereby in contrast to the configuration of FIG. 3 the thumb of the operator is now laid on the roller 50 and the thread is moved reciprocally by means of the roller 50.

The thread 70 lies in the slot 58 between both silicon O-rings 54 and 56, creating intensive contact. The position of the arm 24 of FIG. 4 now corresponds to the position of FIG. 2, i.e. the arm 24 is catched and cannot be pressed back further into the recess 68.

If the catching force is overcome the arm 24 rises such that then the device 10 for example is again withdrawn from the cylindrical extension 76 when the arm 24 is grasped, or vice versa can be clipped thereon in this position, for example.

It is evident from the plan view of FIG. 5 that the thread 70 is guided in a gutter 74 aligned with the slot 58. If for example a thread having an extremely smooth outer surface is to be worked with and due to the operating procedure it cannot be ruled out that the hand or respectively the latex glove is moist, the handling of the thread, that is to say the reciprocal motion, can be made substantially easier by putting on the device 10 and especially proceeding with a substantially better handling feel.

The device 10 can be withdrawn again following the handling procedure.

The roller 50 can be pressed up out of the grooves 38 and 40 of the retaining arms 44, 36 for cleaning, allowing cleaning to then proceed easily. Provision can also be made for designing the roller 50 as a disposable item, where another new roller 50 is then clipped in for a subsequent operating procedure.

This also offers the possibility of putting on variously configured rollers 50 with variously configured threads, in particular with a different configuration of the peripheral area, as is yet to be described hereinbelow.

FIG. 6 illustrates a second embodiment of a device 10' which is designed in terms of its principal components identically to the device 10 illustrated in FIGS. 1 and 2 to the extent where the same reference numerals are accordingly also used for these same components.

In contrast to the device 10 illustrated in FIGS. 1 and 2 the device 10' in each case has projections 82 standing out from the legs 16 or respectively 18 in the direction of the roller 50, which constitute a lock against rotation whenever the device 10' is clipped onto a rod-like body 62 which has a relatively round profile.

In the third embodiment of a device 90 according to the invention illustrated in FIGS. 7 and 8 the latter likewise has, as described in connection with FIGS. 1 and 2, a clamp 92 on which an arm 94 is attached pivotably about an axis 98. Here, too, the arm 94 bears a roller 96.

By comparison to the device 10 illustrated in FIGS. 1 and 2 here the arm 94 can pivot freely, and not against the force of a spring. Neither is a catch provided here, such that the operator is free to press the arm 94 or respectively the roller 96 onto the thread using force he chooses.

This variant is to be employed if the operator actually does want this method, that is to say if the operator him/herself would like to determine how much pressure is to be exerted by the roller 96 on the thread.

The device of FIGS. 7 and 8 can also accordingly be clipped onto a device illustrated in FIG. 3. FIG. 8 shows that the peripheral surface 100 is provided universally with a lining 102 of a material with a high friction, for example a band made of silicon rubber.

As is evident from the plan view of FIG. 5, the thread 70 is guided in a gutter 74, such that also without a slot on the peripheral area of the roller 96 relatively lateral shift-free reciprocal motion of the thread is possible, specifically when the peripheral band on the friction-fast lining 102 is pressed full-surface onto the thread 70.

Figure 10:
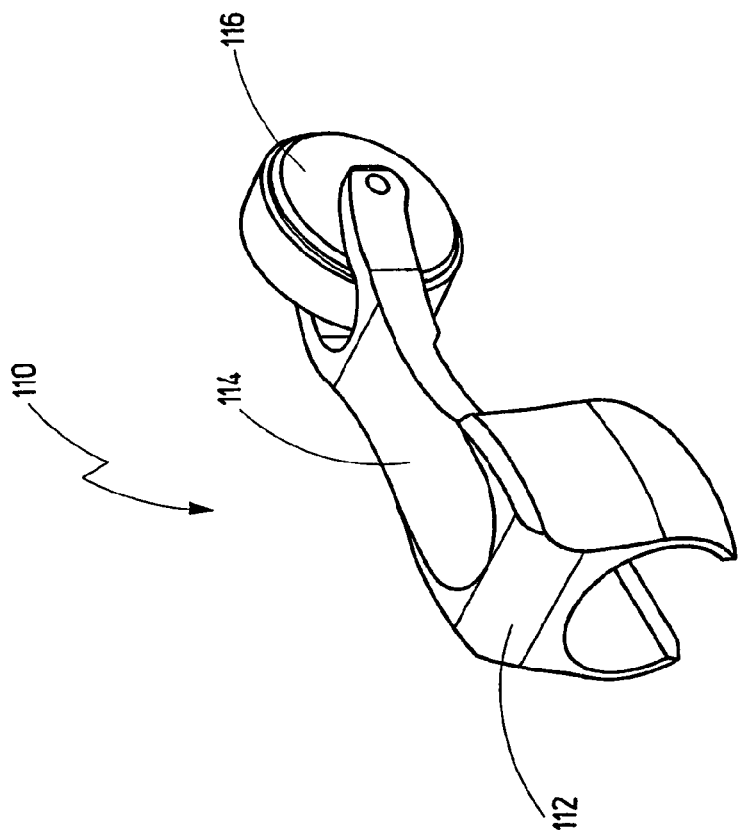
FIG. 10 shows a perspective view of the embodiment of FIG. 9.
Figure 9:
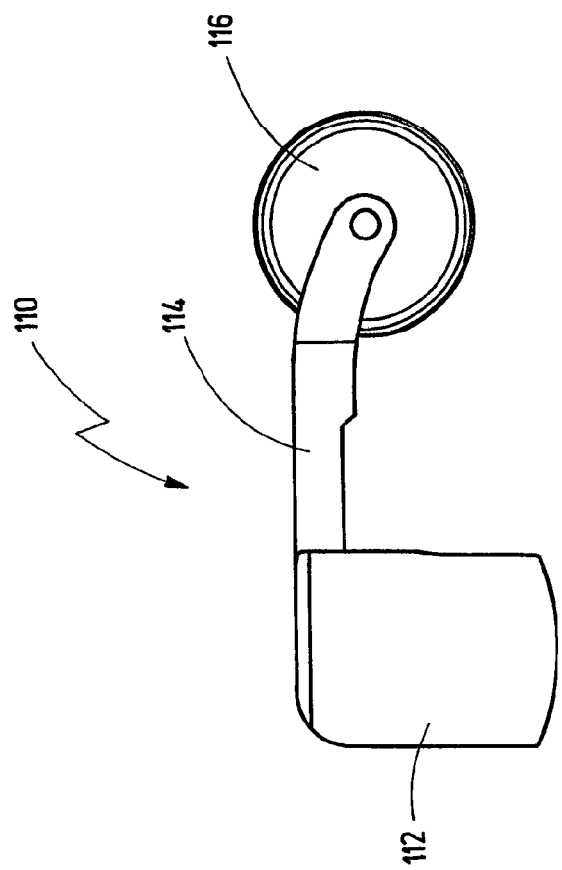
FIG. 9 shows a side elevation corresponding to the illustration of FIG. 7 of a fourth embodiment with a rigid, therefore non-pivotable arm.

FIGS. 9 and 10 illustrate a fourth embodiment of a simplified device according to the invention 110. The device 110 also has a clamp 112, described as previously, on which however an arm 114 is attached rigidly and immovably, bearing a roller 116. Also, the device 110 can be clipped onto the surgical sewing device of FIG. 3 for example. Since here the arm 114 cannot be pivoted the geometry of clamp 112 and arm 114 as well as the geometry of the roller 116 must be coordinated on the surgical sewing device 60 such that after clipping on it is assured that the peripheral area of the roller 116 rests on the thread.

If for example the device of FIGS. 9 and 10 is therefore offered as a set together with the device of FIG. 3, measures can already be taken by the manufacturer to ensure that the previously stipulated requirements have respectively been fulfilled.

In this case the device 110 is then to be manufactured as a simple injection-moulded plastic item, with only the roller 116 still having to be inserted.

This offers the possibility of manufacturing the entire device 110 as a one-off part or respectively a disposable part.

What is claimed is:

1. A device for moving a thread of a surgical sewing instrument, said sewing instrument having an approximately rod-like body, wherein a thread can be fed through an interior of said approximately rod-like body from proximal to distal, said approximately rod-like body having a hollow that laterally exposes a section of said thread to an exterior within said hollow, thereby allowing said exposed section of said thread to be moved by a finger of a hand gripping said rod-like body, said device comprising
   a clamp for detachably clipping said device on to an outer side of said rod-like body of said surgical sewing instrument,
   an arm having a first end connected to said clamp,
   a freely rotatable roller being arranged at a second end of said arm, said roller resting on a thread section freely exposed in said hollow when said device being clipped on, allowing a finger of a hand gripping said rod-like body to move said thread via said roller resting on said thread by turning said roller.

2. The device of claim 1, wherein said roller is attached removable to said arm.

3. The device of claim 1, wherein said roller is held in two retaining arms of said arm.

4. The device of claim 3, wherein a groove is provided in each of said two retaining arms into which grooves ends projecting from both sides of a bearing shaft bearing said roller can be clipped.

5. The device of claim 1, wherein said roller is being clipped into said arm.

6. The device of claim 1, wherein a peripheral surface area of said roller is provided with a material of high friction.

7. The device of claim 1, wherein a peripheral surface of said roller is provided with a circumferential slot for accommodating a thread of a surgical sewing instrument.

8. The device of claim 7, wherein said circumferential slot is provided between two O-rings disposed on said peripheral surface of said roller.

9. The device of claim 1, wherein said arm is attached pivotably to said clamp.

10. The device of claim 9, wherein said pivotable arm can be pivoted against a force of a spring.

11. The device of claim 9, wherein said pivotable arm can be fixed by a catch provided at said clamp.

12. The device of claim 1, wherein said clamp has a lock preventing a rotation of said clamp when clipped on to a surgical sewing instrument.

13. The device of claim 12, wherein said lock is designed by projections standing out from said clamp.

14. A surgical sewing instrument having an approximately rod-like body, wherein a thread can be fed through an interior of said approximately rod-like body from proximal to distal, said approximately rod-like body having a hollow that laterally exposes a section of said thread to an exterior within said hollow, thereby allowing said exposed section of said thread to be moved by a finger of a hand gripping said rod-like body, and a device for moving said thread of said surgical instrument, said device comprising
   a clamp for detachably clipping said device on to an outer side of said rod-like body of said surgical sewing instrument,
   an arm having a first end connected to said clamp,
   a freely rotatable roller being arranged at a second end of said arm, said roller resting on a thread section freely exposed in said hollow when said device being clipped on, allowing a finger of a hand gripping said rod-like body to move said thread via said roller resting on said thread by turning said roller.

15. The surgical sewing instrument of claim 14, wherein said roller is attached removable to said arm.

16. The surgical sewing instrument of claim 14, wherein said roller is held in two retaining arms of said arm.

17. The surgical sewing instrument of claim 14, wherein said roller is being clipped into said arm.

18. The surgical sewing instrument of claim 14, wherein a groove is provided in each of said two retaining arms into which grooves ends projecting from both sides of a bearing shaft bearing said roller can be clipped.

19. The surgical sewing instrument of claim 14, wherein a peripheral surface area of said roller is provided with a material of high friction.

20. The surgical sewing instrument of claim 14, wherein a peripheral surface of said roller is provided with a circumferential slot for accommodating said thread of said surgical sewing instrument.

21. The surgical sewing instrument of claim 14, wherein said circumferential slot is provided between two O-rings disposed on said peripheral surface of said roller.

22. The surgical sewing instrument of claim 14, wherein said arm is attached pivotably to said clamp.

23. The surgical sewing instrument of claim 14, wherein said pivotable arm can be pivoted against a force of a spring.

24. The surgical sewing instrument of claim 14, wherein said pivotable arm can be fixed by a catch provided at said clamp.

25. The surgical sewing instrument of claim 14, wherein said clamp has a lock preventing a rotation of said clamp when clipped on to said surgical sewing instrument.

26. The surgical sewing instrument of claim 25, wherein said lock is designed by projections standing out from said clamp.

* * * * *